United States Patent [19]

Neef et al.

[11] Patent Number: 5,089,635

[45] Date of Patent: Feb. 18, 1992

[54] 11 BETA-PHENYL-GONANES, THEIR MANUFACTURE AND PHARMACEUTICAL PREPARATIONS CONTAINING THEM

[75] Inventors: Günter Neef; Sybille Beier; Walter Elger; David Henderson; Eckard Otto; Ralph Rohde, all of Berlin, Fed. Rep. of Germany

[73] Assignee: Schering Aktiengesellschaft, Berlin and Bergkamen, Fed. Rep. of Germany

[21] Appl. No.: 827,050

[22] Filed: Feb. 7, 1986

[30] Foreign Application Priority Data

Feb. 7, 1985 [DE] Fed. Rep. of Germany ....... 3504421
Jul. 29, 1985 [DE] Fed. Rep. of Germany ....... 3527517

[51] Int. Cl.$^5$ .................... C07D 307/77; A01N 45/00
[52] U.S. Cl. ..................................... 549/297; 549/305; 549/544; 560/255; 564/265; 568/329; 568/439
[58] Field of Search ................ 514/169; 549/297, 305, 549/544; 560/255; 564/265; 568/329, 439

[56] References Cited

U.S. PATENT DOCUMENTS 4,233,296 11/1980 Teutsch et al. .
4,386,085 5/1983 Teutsch et al. .
4,447,424 5/1984 Teutsch et al. ................... 514/179
4,634,695 1/1987 Torelli et al. ..................... 514/178

FOREIGN PATENT DOCUMENTS 0104387 4/1984 European Pat. Off. .
184471 6/1986 European Pat. Off. .
190759 8/1986 European Pat. Off. .
3307143 9/1983 Fed. Rep. of Germany .

Primary Examiner—Paul J. Killos
Attorney, Agent, or Firm—Millen, White & Zelano

[57] ABSTRACT

13-alkyl-11β-phenyl-gonanes of general formula I

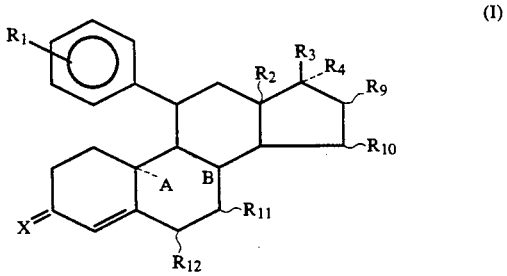

wherein

A and B together stand for an oxygen atom, a $CH_2$ group or a second bond between carbon atoms 9 and 10, X is an oxygen atom or the hydroxyimino grouping N~OH, $R_1$ is a straight-chained or branched, saturated or unsaturated alkyl radical with up to 8 carbon atoms, which contains the grouping

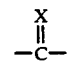

with X as described above, $R_2$ is a methyl or ethyl radical in the α or β position, $R_9$, $R_{10}$, $R_{11}$ and $R_{12}$ each stand for a hydrogen atom, a hydroxy, alkyl, alkoxy or acyloxy group with 1 to 4 carbon atoms respectively or a halogen atom and $R_3$ and $R_4$ have a variety of meanings, have antigestagenic and antiglucocorticoid effects.

45 Claims, No Drawings

11 β-PHENYL-GONANES, THEIR MANUFACTURE AND PHARMACEUTICAL PREPARATIONS CONTAINING THEM

BACKGROUND OF THE INVENTION

This invention relates to new 11β-phenyl-gonanes, processes for their manufacture and pharmaceutical preparations containing them. 11β-phenyl steriods are already known. Thus, for example 11β-aryl-17α-propinyl- and ethinyl-4,9(10)estradienes are described in European Patent Application 82400025.1 (U.S. Pat. Nos. 4,386,085 and 4,447,424) and 4,386,085, 11β-phenyl-17α-(3-hydroxypropyl)4,9(10)-estradienes in European Patent Application 84101721.3 (U.S. Pat. No. 4,536,401) 11β-phenyl-17α-(3-hydroxpropyl-1-enyl)-4,9(10)-estradienes in European Patent Application 84730147.0 (U.S. Ser. No. 685,088) and 17β-hydroxy-17α-(3-hydroxypropyl)-respectively 17α-hydroxy-17β-(3-hydroxypropyl)-13 α-methyl-4,9-gonanes in European Patent Application 84730062.1 (U.S. Ser. No. 621,308). These compounds have a strong affinity for gestagen receptors without themselves possessing gestagenic activity. They are competitive antagonists of progesterone (antigestagens) and are suitable for inducing abortion since they displace from the receptor the progesterone required to maintain pregnancy. They are therefore valuable and interesting with regard to their use as a postcoital fertility control means. They can also be used to treat hormonal irregularities, to bring on menstruation and induce birth. The compounds set out in European Patent Application 84101721.3 and 84730147.0 also have antimineral-corticoid effects in addition to their antigestagenic properties.

On the other hand, the 11β-aryl-17α-propinyl- and ethinyl-4,9(10)estradienes first mentioned display antiglucocorticoid activity and can thus be used as pharmaceuticals for therapy of corticoid-induced disorders (glaucoma) and to combat side effects that occur during long-term treatment with glucocorticoids (Cushing's syndrome). They therefore also make it possible to combat disorders due to a supersecretion of glucocorticoids, above all adipositas, arteriosclerosis, osteoporosis, diabetes and insomnia.

However, so far there has been no success in achieving a desirable extent of dissociation between antigestagenic and antiglucocorticoid effects of these compounds (G. Teutsch in "Adrenal Steroid Antagonism", Walter de Gruyter Berlin-New York, 1984, p. 43).

SUMMARY OF THE INVENTION

It is thus an object of this invention to provide compounds useful as medicaments, particularly having the mentioned desirable dissociation of activities.

Upon further study of the specification and appended claims, further objects and advantages of this invention will become apparent to those skilled in the art.

It has now been discovered that the new compounds of general Formula I surprisingly display not only very good antigestagenic and antiglucocorticoid effects but also a differentiation of the two effects. Thus, the compounds of this invention are of Formula I:

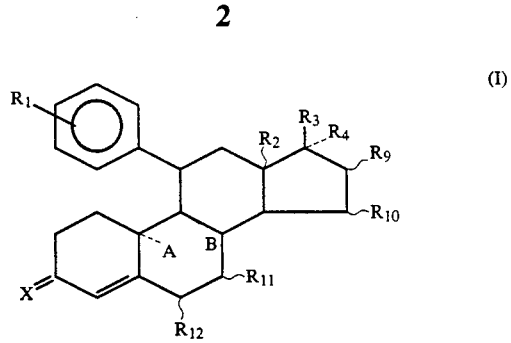

where
A and B together represent an oxygen atom, a $CH_2$ group or a second bond between carbon atoms 9 and 10,
X is an oxygen atom or the hydroxyimino group N~OH,
$R_1$ is a straight-chained or branched, saturated or unsaturated hydrocarbon aliphatic group (i.e., alkyl, alkenyl or alkynyl) with up to 8 carbon atoms, each of which contains the grouping $$\begin{matrix} X \\ \| \\ -C- \end{matrix},$$

wherein X is as defined above,
$R_2$ is methyl or ethyl in α or β position,
wherein, in the case of $R_2$ methyl or ethyl in the α-position:
$R_3/R_4$ is $-OR_5/-C\equiv C-Y$ $-C\equiv C-Y/-OR_5$ $-OR_5/-\underset{O}{\underset{\|}{C}}-CH_2-R_6$ $-\underset{O}{\underset{\|}{C}}-CH_2R_6/-OR_5$ $-CH_3/-\underset{O}{\underset{\|}{C}}-CH_2-R_6$ $-\underset{O}{\underset{\|}{C}}-CH_2-R_6/-CH_3$ $-H/-\underset{O}{\underset{\|}{C}}-CH_2-R_6$ $-\underset{O}{\underset{\|}{C}}-CH_2-R_6/-H$ $-OR_5/-(CH_2)_m-CH_2-R_7$ $-(CH_2)_m-CH_2-R_7/-OR_5$ $-OR_5/-CH=CH-(CH_2)_k-CH_2-R_7$ $-CH=CH-(CH_2)_k-CH_2-R_7/-OR_5$ $-OR_8/-H$ $-H/-OR_8$ -continued

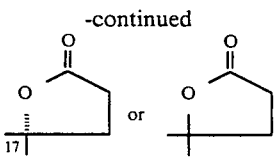

and where, in the case of $R_2$ methyl or ethyl in the β-position:
$R_3/R_4$ is

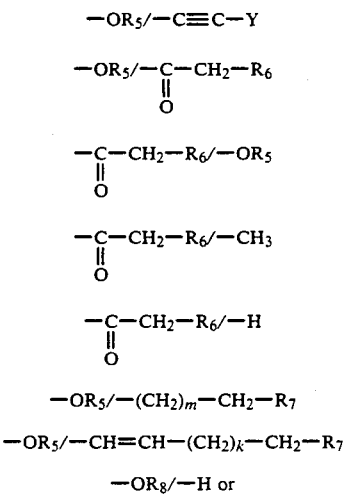

$$-OR_8/-H \text{ or}$$

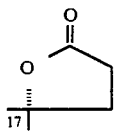

$R_5$ is a hydrogen atom or an acyl radical of 1 to 4 carbon atoms,

Y is a hydrogen, chlorine, fluorine, iodine or bromine atom, or an alkyl, hydroxyalkyl, alkoxyalkyl or acyloxyalkyl group each of 1 to 4 carbon atoms in each alkyl or acyl group, $R_6$ is a hydrogen atom, a hydroxy group, an alkyl, O-alkyl or O-acyl group each of 1 to 4 carbon atoms, m is 0, 1, 2 or 3, $R_7$ is hydroxy or cyano or O-alkyl or O-acyl each of 1 to 4 carbon atoms, k is 0, 1 or 2, $R_8$ is a hydrogen atom or an alkyl or acyl group of 1 to 10 carbon atoms each, each of $R_9$, $R_{10}$, $R_{11}$ and $R_{12}$ independently is a hydrogen atom, an hydroxy group, an alkyl, alkoxy, acyloxy group each of 1 to 4 carbon atoms or a halogen atom, and the substituent of the 11β-phenyl radical is in position 3 or 4.

This invention also relates to corresponding pharmaceutical compositions and methods of use.

DETAILED DISCUSSION

The abortive effect was determined to distinguish the antigestagenic effect.

The experiments were performed on rats weighing approximately 200 g. After mating, the beginning of pregnancy was ascertained by demonstrating the presence of sperm in vaginal smears. The day on which the presence of sperm was verified is considered the first day of pregnancy (=d1 p.c.). After nidation of the blastocysts from d5 p.c. to d7 p.c., the animals were treated with the respective substance and/or solvent to be tested. On d9 p.c. the animals were killed and the uteri examined for implants and places of resorption. Photographs were made of all the uteri. The absence of implants was evaluated as an abortion.

The test substances were dissolved in a mixture of benzyl benzoate and castor oil (ratio of 1:9). The vehicle volume per individual dose amounted to 0.2 ml. Treatment was subcutaneous (s.c.).

The superiority of the compounds in accordance with the invention will be demonstrated by comparing the biological properties of the compounds in accordance with the invention, the 11β-(4-acetylphenyl)-17β-hydroxy-17α-(1-propinyl)-4,9-estradien-3-one (A), 17β-hydroxy-17α-(3-hydroxy-1(Z)-propenyl)-11β-(4-propionyl-phenyl)-4,9-estradien-3-one (B) and 11β-(4-acetylphenyl)-17β-hydroxy-17α-(3-hydroxy-1(Z)-propenyl)-4,9-estradien-3-one (C) with the 11β-(4-dimethylaminophenyl)-17β-hydroxy-17α-(propin-1-yl)-4,9)(10)-estradien-3-one RU 38486 described in European Patent 82400025.1 (D), the 11β-(4-dimethylaminophenyl)-17β-hydroxy-17α- (3-hydroxy-propyl)-4,9(10)-estradien-3-one (E) in EP 84101721.3, the 11β-(4-dimethylaminophenyl)-17β-hydroxy-17α-(3-hydroxy-prop-1(Z)-enyl)-4,9(10)-estradien-3-one (F) described in EP 84730147.0 and the 11β-(4-dimethylaminophenyl)-17β-hydroxy-17α-(3-hydroxypropyl)-13α-methyl-4,9-gonadien-3-one (G) as well as the 11β-(4-dimethylaminophenyl-17α-hydroxy-17β-(3-hydroxypropyl)-13α-methyl-4,9-gonadien-3-one (H) described in European Patent EP 84730062.1.

TABLE 1

| | Abortion Test with Pregnant Rats | |
|---|---|---|
| Substance | Dose mg/animal/day s.c. | Abortion Rate n abortion positive/n total |
| A This | 3.0 | 4/4 |
| Invention | 1.0 | 4/4 |
| | 0.3 | 4/4 |
| B This | 3.0 | 4/4 |
| Invention | 1.0 | 4/4 |
| | 0.3 | 4/4 |
| | 0.1 | 4/4 |
| C This | 3.0 | 4/4 |
| Invention | 1.0 | 4/4 |
| | 0.3 | 4/4 |
| | 0.1 | 4/4 |
| D Prior | 10.0 | 4/4 |
| Art | 3.0 | 4/4 |
| | 1.0 | 2/4 |
| | 0.3 | 0/4 |
| E Prior | 10.0 | 4/4 |
| Art | 3.0 | 4/4 |
| | 1.0 | 0/4 |
| F Prior | 10.0 | 4/4 |
| Art | 3.0 | 4/4 |
| | 1.0 | 4/4 |
| | 0.3 | 0/4 |
| G Prior | 10.0 | 4/4 |
| Art | 3.0 | 4/4 |
| | 1.0 | 4/4 |
| | 0.3 | 0/4 |
| H Prior | 10.0 | 4/4 |
| Art | 3.0 | 4/4 |
| | 1.0 | 4/4 |
| | 0.3 | 0/4 |

From Table 1 it can be seen that only the compounds in accordance with the invention have a fully abortive effect at a dose of 0.3 (A) and 0.1 mg (B,C), i.e., they are more effective than the state-of-the-art compounds by a factor of 3 to 30.

The influence on the tyrosine aminotransferase of the substances in accordance with the invention was ascertained to distinguish the antiglucocorticoid effect. The test system is based on a measurement of the activity of the liver enzyme tyrosine aminotransferase (TAT) in cultures of RHC (rat hepatoma cells). The enzyme catalyzes the first step in the metabolism of tyrosine and can be induced by glucocorticoids in both the liver and hepatoma cells. The activity is easy to measure in crude extracts (Granner and Tomkins, (1970) Meth. Enzymol. 15, 633). The enzyme converts the amino group of tyrosine to 2-oxo-glutaric acid. This results in glutaminic acid and p-hydroxyphenyl pyruvate. In an alkaline solution the more stable p-hydroxybenzaldehyde is formed from the p-hydroxyphenyl pyruvate, the absorption of the former being measured at 331 nm. The TAT activity in RHC cells displays a dose-dependent induction with cortisol (max. activity at $10^{-6}$M) or dexamethasone (max. activity at $10^{-7}$M). It is possible to stimulate activity by a factor of 4 to 6 by acting on the basal rate. Simultaneous treatment with corticoid and antiglucocorticoid leads to a decrease in TAT activity.

In this test compound A in accordance with the invention displays 30%, compounds B and C in accordance with the invention less than 1% of the activity of RU 38.486 (D), a substance that can be viewed as standard (7th International Congress of Endocrinology, July 1-7, 1984, Quebec City, Canada; Excerpta Medica, Amsterdam-Oxford-Princeton).

Since compound (A) is 10 times more antigestagenic than (D), and compounds (B) and (C) 30 times more antigestagenic, there is thus a clear dissociation of the antiglucocorticoid and antigestagenic properties.

Another example in accordance with the invention that should be mentioned is 11β-[4-(anti-hydroxyiminomethyl)-phenyl]-17β-hydroxy-17α-(1-propinyl)-4,9-estradien-3-one-anti-oxime (J); this compound displays an antiglucocorticoid effect similar to that of (D). But in the antigestagen test the effect is at least 10 times weaker than that of (D).

In the gestagen-receptor binding test the affinity of the compounds in accordance with the invention for the gestagen receptor is investigated. The displacement of the agonist by the antagonist is measured in this connection.

Use is made of the cytosol from rabbit-uterus homogenate, which contains the receptor molecule—a protein. This binds progesterone with high affinity and low capacity. If these receptors are loaded with $^3$H-progesterone in the presence of the unmarked substance to be tested, the degree to which the $^3$H-progesterone is displaced from the receptor depends on the concentration and the binding affinity of the compound to be tested. After separation of the progesterone bound to the receptor from the non-bound progesterone it is possible to obtain the binding in percent and to plot this value against the logarithm of the molar concentration of the substance being tested. Characteristic dose-dependent displacement curves are obtained and it is now possible to ascertain the concentration of the test substance which is required to completely displace the reference substance from the receptor. The competition factor K, the yardstick for the binding power, is defined as the ratio of the concentration of the test substance to the concentration of the reference substance (progesterone), in the case of which both compounds display equally great displacement of $^3$H-progesterone from the progesterone-receptor complex, so that a low K-value indicates high binding power (high affinity).

TABLE 2

| Gestagen Receptor Binding Test | |
|---|---|
| Compound | Rabbit Uterus K (Gestagen) |
| A | 1.0 |
| B | 1.6 |
| C | 0.7 |
| D (Prior Art) | 2.9 |
| I | 1.5 |
| K | 2.1 |
| L | 2.6 |
| M | 0.9 |

The table shows that compounds A, B, C in accordance with the invention and given as examples, namely 11β-(4-formylphenyl)-17β-hydroxy-17α-(1-propinyl)-4,9-estradien-3-one (I) 17β-hydroxy-17α-(1-propinyl)-11β-(4-propionyl-phenyl)-4,9-estradien-3-one (K), 11β-4(acetylphenyl)-17β-hydroxy-9α, 10α-methylene-17α-(1-propinyl)-4-estren-3-one (L) and 3-[11β-(4-acetylphenyl)-17β-hydroxy-3-oxo-4,9-estradien-17α-yl]-propionic acid lactone (M) are as much as 4 times more effective in the gestagen-receptor binding test than the compound (D) considered standard.

The invention also relates to pharmaceutical preparations containing compounds of general formula I useful, e.g., to treat mammals including humans. The pharmacologically effective compounds of general formula I in accordance with the invention can be processed by the generally known galenical methods into pharmaceutical preparations for enteral, percutaneous or parenteral application.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10-100 mg in a pharmaceutically acceptable carrier per unit dosage. The dosage of the antigestagenic compounds according to this invention generally is about 1-1,000 mg/day when administered to patients, e.g., humans preferably 5-200 mg/day to the known agent RU 486. The dosage of the compounds of this invention generally is 1-500 mg/day when adminstered to such patients, preferably 1-100 mg/day, to treat, e.g., Cushing Syndrome. Suitable dosage and regimens for a given host can be determined using conventional considerations, e.g., by customary comparison of the differential activities of the subject compound and of a known agent, e.g., by means of an appropriate, conventional pharmacological protocol.

All compounds of this invention will have at least one of the antiglucocordicoidal or antigestagenic activities of this invention. The activity spectrum for a given compound can be routinely determined with no undue experimentation, e.g., using conventional pharmacological protocols, e.g., those described herein. Without intending to limit the scope of this invention in any way, it can be stated that a 17-hydroxypropenyl side chain generally decreases antiglucocordicoidal activity in comparison, e.g., to that of the prior art 17-propinyl side-chain-containing compounds. Further, a $9\alpha, 10\alpha$-$CH_2$ group generally decreases the antiglucocordicoidal activity. The oxime structure generally lowers the antigestagenic activity.

The alkyl groups contained in $R_1$ of general formula I may have as many as 8, preferably up to 4, carbon atoms. Suitable alkyl portions in all groups (e.g., alkyl, alkoxy, acyl, acyloxyalkyl, etc.) can be selected from methyl, ethyl, i- or n-propyl, n-, i-, s- or t-butyl, or for $R_1$ also possibly a pentyl, hexyl, heptyl or octyl group, or for $R_8$ also possibly a nonyl or decyl group. In the case of the saturated $R_1$ alkyl radical substitutions, it is preferred that the

group is directly connected to the phenyl ring, e.g., preferred are, e.g., the formyl, acetyl, propionyl and butyryl groups or their hydroxyimino derivatives. In the case of the $R_1$ unsaturated aliphatic radicals, i.e., alkenyl or alkynyl groups of 3-8 C-atoms, $\alpha, \beta$ unsaturated

groupings, in which C-atoms 1 and 2 of the chain carry the double bond, are preferred.

In all alkyl-containing groups, preferred groups are methyl, ethyl, propyl, formyl, acetyl, propionyl, butyryl, methoxy and ethoxy, where appropriate. Preferred acyl groups are alkanoyl groups.

Of the alkenyl radicals, the propenyl group, which can be in the E or Z configuration, is preferred. Thus, when $R_4$ is $-CH=CH-(CH_2)_k-CH_2-R_6$, k preferably is zero. When $R_9, R_{10}, R_{11}$ or $R_{12}$ are halogen, chlorine is preferred.

In the case of substituents $R_9, R_{10}, R_{11}$ and $R_{12}$, monosubstitution is preferred, i.e., three of these substituents preferably are hydrogen atoms.

The new 13-alkyl-11$\beta$-phenyl-gonanes of general formula I are prepared in accordance with this invention by a method comprising in a manner known in the art, exposing a compound of general formula II to a dehydrating agent:

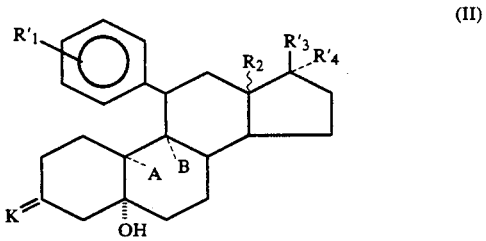

wherein K is a blocked ketone group in the form of a ketal, thioketal, oxime or methyloxime, A, B and $R_2$ are as defined above, $R'_1$ is as defined above for $R_1$ but contains a

instead of

group, $R'_3$ has the same meaning as $R_3$ but any hydroxy groups being conventionally protected, and $R'_4$ has the same meaning as $R_4$, but any hydroxy or acyl groups being conventionally protected, and $K_l$ also stands for a hydrogen atom and a protected hydroxy group in addition to the aforementioned meanings of K, the dehydrating agent also being capable of releasing the protected function(s), thereby separating water while simultaneously forming the 4(5) double bond, oxidizing a hydroxy group contained in $K_l$, optionally, for the compounds of general formula I thus obtained, with $R_9, R_{10}, R_{11}$ and $R_{12}$ in each case being hydrogen atoms, reacting them by microbiological hydroxylation with micro-organisms of the species *Streptomyces toyocaensis* (DSM 40030) and/or *Streptomyces platensis* (NRRL 2364) and/or *Nigrospora sphaerica* (CBS 98469) and/or *Neurospora crassa* (ATCC 9278), optionally, for the hydroxylated compounds of the general formula I thus obtained, where at least one of the substituents $R_9, R_{10}, R_{11}$ and $R_{12}$ is an hydroxy group, the remaining substituents being hydrogen, epimerizing them at the positions carrying the hydroxy groups, and/or further optionally for these hydroxy groups, etherifying, esterifying or replacing them by a halogen or alkyl radical, optionally for the hydroxy groups present in $R_3$ and $R_4$, esterifying or etherifying them to form a product of general formula I where X is an oxygen atom and, further optionally, subsequently reacting them with hydroxylamine hydrochloride in the presence of tertiary amines at temperatures of between $-20°$ C. and $+40°$ C.

Starting with the compounds of general formula II, these compounds are treated with acid or an acid ion exchanger to split off water while forming the 4(5) double bond and simultaneously remove any protected groups. The acid treatment is performed in the way known in the art inasmuch as the compound of formula II, which contains at least two protected groups, is dissolved in a solvent mixable with water, like aqueous methanol, ethanol or acetone, and the solution is allowed to react with catalytic amounts of mineral or sulfonic acid, like hydrochloric acid, sulfuric acid, phosphoric acid, perchloric acid or p-toluene sulfonic acid, or an organic acid, like acetic acid, until the water has split off and the protected groups removed. The reaction, which takes place at temperatures of 0° to 100° C., can also be undertaken with an acid ion exchanger. The course of the reaction can be followed by analytical methods, for example by thin-layer chromatography of samples.

In an acid medium the protected groups comprised of K, $K_1$, $R'_3$ and $R'_4$ in general formula II are easily splittable groups like, for example, the ethylenedioxyketal, ethylenedithioketal, 2,2-dimethyl-trimethylenedioxyketal, hydroxyimino, methoxyimino, tetrahydropyranyl, methoxymethyl or ethoxymethyl group.

If a compound of general formula II is used, the $K_I$ of which contains a protected hydroxy group, it is subsequently converted into the oxo function by an oxidizing agent customary for the oxidation of allylic hydroxy groups such as, for example, chromic acid, pyridine, pyridinium dichromate, pyridinium chlorochromate, manganese dioxide, silver carbonate on Celite. Conversion with manganese dioxide at temperatures between $-20°$ C. and $+40°$ C. is preferred.

The hydroxy groups are introduced into positions 6, 7, 15 and 16 of the steroid structure of general formula II, with $R_9$, $R_{10}$, $R_{11}$ and $R_{12}$ in the respective meaning of one hydrogen atom, with the help of microorganisms.

Thus there is a 6α-hydroxylation if microorganisms of the species Nigrospora sphaerica(CBS 98469) are used for the fermentation. 7α-hydroxylation is possible with Neurospora crassa (ATCC 9278), 15β with Streptomyces platensis (NRRL 2364) and 16α-hydroxylation with Streptomyces toyocaensis (DSM 40030).

The fermentations are carried out under the conditions customarily used in the microbiological hydroxylation of steroids with microorganisms. Thus, in customary preliminary experiments the enzyme of the microorganism is analytically examined, especially by thin-layer chromatography, to first ascertain the best fermentation conditions such as, for example, selection of the best nutrient medium, the appropriate substrate solvent or suspension agent, the substrate concentration, technical conditions such as temperature, aeration, pH-value and optimum times for germination, addition of substrate and substrate contact.

It is advisable to apply the substrate in a concentration of approximately 100 to 5000 mg per liter of nutrient medium. The pH-value is preferably set at a range of 5 to 7.5. The growing temperature is from 20° to 40° C., preferably from 25° to 35° C. 0.5 to 5 liters of air per minute per liter of culture are preferably fed in for aeration. It is advisable to follow conversion of the substrate by analysis with thin-layer chromatography. The fermentation takes approximately 30 to 130 hours.

The configuration of these secondary alcohols is reversed by the generally known methods, preferably by way of the Mitsunobu reaction with azodicarbonic acid ester/triphenylphosphine. (Synthesis 1981, 1. Chem. Commun. 1981, 840).

The halogen substituents are introduced into the C-6, C-7, C-15 or C-16 position of the steroid structure in accordance with the methods known in the literature by nucleophilic substitution of the corresponding hydroxy groups together with inversion, preferably with triphenyl phosphine and a halogen source such as, for example $CCl_4$ or $CBr_4$ (Chem. Ind. 1966, 900, Can. J. Chem. 1982, 210, J. C. S. Perkin I 1982, 681 Synthesis 1983, 139) or in the case of the fluoride substituent with (diethylamino) sulfur trifluoride (U.S. Pat. No. 3,914,265, J. Org. Chem. 1983, 393).

If introduction of a C-6, C-7, C-15 or C-16 alkyl is desired, use is likewise made of the corresponding hydroxylated educts. After conversion to an appropriate volatile group such as, for example, mesylate, tosylate, iodide, bromide, but preferably tosylate, the hydroxy group is replaced by conversion with lithium dialkylcuprates or organocuprates of the formula alkyl$_2$Cu(CN)Li$_2$ (J. Am. Chem. Soc. 103, 7672 (1981)).

If desired the compounds of general formula I, with X in the meaning of an oxygen atom, can be converted by reaction with hydroxylamine hydrochloride in the presence of tertiary amines at temperatures between $-20°$ and $+40°$ C. into oximes (formula I, with X in the meaning of the hydroxyimino grouping N~OH, it being possible for the hydroxy group to be in the syn or anti position). Suitable teriary bases are, for example, trimethylamine, triethylamine, pyridine, N,N-dimethylaminopyridine, 1,5-diazabicyclo[4.3.0]nonene-5 (DBN) and 1,5-diazabicyclo[5.4.0.]undecene-5 (DBU), pyridine being preferred.

If esterification of the compounds of general formula I is desired, in which $R_3$, $R_4$, $R_9$, $R_{10}$, $R_{11}$ and $R_{12}$ contain a hydroxy group, the acylation is done in the manner known in the art, for example, by converting with acid anhydride in pyridine at room temperature.

The manufacture of the initial compounds of general formula II starts, as described for example in European Patent Applications 84101721.3 and 82400025.1, with the epoxide of general formula III

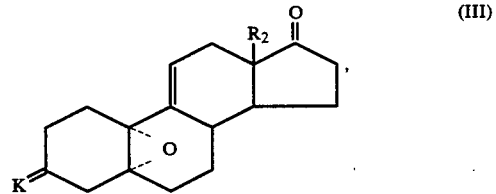

where $R_2$ is in the β position.

The 11β-phenyl radical is introduced, with formation of the $\Delta^{9,10}$-5α-hydroxy structural element, either by means of a Grignard reaction catalyzed with Cu(I), with the corresponding aryl magnesium halogenides (Tetrahedron Letters 1979, 2051), or by reaction with the mixed organocuprates of type $R_2$ Cu(CN)Li$_2$ (J. Amer. Chem. Soc. 103 (1981) 7672).

Access to the 13α-methyl or 13α-ethyl series ($R_2$ is in the α-position) is gained—as described for example in European Patent Application 84730062.1 by irradiating the intermediate products of general formula IV

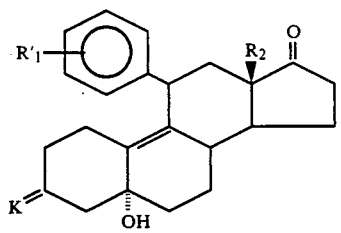 (IV)

with ultraviolet light.

A 9,10 epoxy or methylene group (A and B together then stand for an oxygen atom or a $CH_2$ group) is introduced at the stage of the $\Delta^{9,10}$-5α,17-dihydroxy-11-β-phenyl phenyl intermediate product according to the methods known, in the art by conversion with, for example, hydrogen, peroxide, organic per-acids like, for example, m-chloroperbenzoic acid or perphthalic acid, tertiary butylhydroperoxide respectively with, for example, methylene iodide or methylene bromide/zink (Simmons-Smith).

The substituents $R_3$ and $R_4$ are introduced in accordance with the customary methods of building a $C_{17}$ side chain by nucleophilic addition to the 17-ketone and subsequent reactions ("Terpenoids and Steroids", Specialist Periodical Report, The Chemical Society, London, Vol. 1–12). While the nucleophile addition to the 17-ketone of the 13β-alkyl series only supplies adducts of the five-ring compound with the hydroxy group in the β-position and the entering group in the α-position, the addition to the corresponding 13-epi-17-ketone generally takes place with the formation of both possible, isomeric forms at C-17, which can, however, be easily separated by chromatography or fractional crystallization. In many cases both isomers are pharmacologically effective, even if the effectiveness can differ.

The nucleophilic addition of HC≡CX, in which x is hydrogen, alkyl with 1 to 4 C-atoms or halogen, is performed with the help of a compound of general formula MC≡CX, in which X has the meaning indicated above and M represents an alkali metal.

The organometallic compound can be formed in situ and made to react with the 17-ketone. Thus, for example, acetylene and an alkali metal, especially potassium, sodium or lithium can be allowed to react with the 17-ketone in a suitable solvent in the presence of an alcohol or in the presence of ammonia. The alkali metal can also be in the form of, for example, methyl- or butyl-lithium. Dialkyl ether, tetrahydrofuran,, dioxane, benzene and toluene are especially suitable as solvents.

To manufacture the 17-chloroethinyl compound, the organometallic chloroethinyl compound is formed in situ from 1,2-dichloroethylene and an etheric alkali metal solution, examples being methyl- or butyllithium solution, and allowed to react with the 17-ketone in solvents like tetrahydrofuran or diethyl ether.

17-bromoethinyl compounds can also be manufactured by brominating the corresponding ethinyl educt (Angw. Chem. 96, 720 (1984)).

The 17-ethinyl-17-hydroxy compounds can be hydrated into the 17-acetyl-17-hydroxy compounds in an alcoholic solution with mercury catalysis (Chem. Ber. 111 (1978) 3086–3093). 3-hydroxypropine,-propene and/or propane are introduced into position 17 by converting the 17-ketone with the metallized derivatives of the propargyl alcohol, e.g. with 1-lithium-3-tetrahydropyran-2'-yloxy-propine-1, into the 17-(3-hydroxy-1-propinyl)-17-hydroxy compounds, which can subsequently be hydrated into the 17-(3-hydroxypropyl and/or 3-hydroxy-propenyl)-17-hydroxy compounds. The hydration must take place in conditions that ensure exclusively an attack on the threefold C—C bond without saturating any existing tetra-substituted 9(10) double bond. This is achieved, for example, by hydrating at room temperature and normal pressure in solvents like methanol, ethanol, propanol, tetrahydrofuran (THF) or acetic ether with the addition of noble-metal catalysts like platinum or palladium.

The homologous hydroxyalkine, hydroxyalkene and hydroxyalkane groups are introduced in corresponding fashion with homologues of the propargyl alcohol.

The compound with the Z-configurated double bond in the hydroxypropenyl group results from hydration of the acetylenic triple bond with a deactivated noble-metal catalyst (J. Fried, J. A. Edwards: Organic Reactions in Steroid Chemistry, Van Nostrand Reinhold Company 1972, p. 134, and H. O. House: Modern Synthetic Reactions 1972, p. 19). Possible deactivated noble-metal catalysts are, for example 10% palladium on barium sulfate in the presence of an amine or 5% palladium on calcium carbonate with the addition of lead (II)-acetate. The hydration is stopped after one equivalent of hydrogen is taken up.

The compound with the E-configurated double bond in the hydroxypropenyl group results from reduction of the acetylenic triple bond in the generally known way. The literature describes a whole number of methods for converting alkines into transolefins, for example reduction with sodium in liquid ammonia (J. Am. Chem. Soc. 63 (1941) 216), with sodium amide in liquid ammonia (J. Am. Chem. Soc. 1955, 3558), with lithium in low-molecular weight amines (J. Am. Chem. Soc. 77 (1955) with boranes (J. Am. Chem. Soc. 93 (1971) 3395 and 94 (1972) 6560), with diisobutyl aluminum hydride and methyllithium (J. Am. Chem. Soc. 89 (1967)5085)and especially with lithium aluminum hydride/alcoholate (J. Am. Chem. Soc. 89 (1967) 4245). Another possibility is reduction of the triple bond with chromium (II) sulfate in the presence of water or dimethylformamide in a weakly acid medium (J. Am. Chem. Soc. 86 (1965) 4358) as well as, in general, reduction by reaction of transition-metal compounds with change of oxidation stage.

If final products of formula I are desired with $R_3/R_4$ in the meaning of

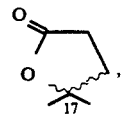

the 17-(3-hydroxypropyl) compound is oxidized in the manner known in the art, for example with Jones' reagent, manganese dioxide, pyridinium dichromate, pyridinium chlorochromate, chromic acid pyridine or the Fetizon reagent silver carbonate/Celite (Compt. rend. 267 (1968) 900).

To introduce the group

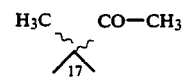

the 17-ketone is converted with tosylmethylisocyanide into the 17-nitrile compound, and methyllithium or methylmagnesium bromide is used to obtain from the 17-nitrile compound the 17-acetyl compound which supplies the desired grouping in position 17 after enolization with K-tert-butylate in tetrahydrofuran and conversion with methyl iodide.

The 17-cyanomethyl side chain is built in the manner known in the art from 17-ketone, for example by way of the 17-spiroepoxide and cracking of the spiroepoxide with HCN in accordance with Z. Chem. 18 (1978) 259-260.

The 17-hydroxyacetyl side chain is also introduced by the generally known methods, e.g. by the method described in J. Org. Chem. 47 (1982), 2993-2995.

Free hydroxy groups in position 6, 7, 15, 16 or 17 can be esterified or etherified in the generally known way.

The strains of *Neurospora crassa* (ATCC 9278), *Nigrospora sphaerica*(CBS 98469), *Streptomyces platensis* (NRRL 2364) and *Streptomyces toyocaensis* are known and, for example, have been deposited in the German collection of microorganisms under numbers DSM 894, DSM 3392, DSM 40041 and DSM 40030.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

17α-ethinyl-11β-(4-formylphenyl)-17βhydroxy-4,9-estradien-3-one

A solution of 9.0 g of 3,3-(2,2-dimethyl-trimethylenedioxy)-11β-[4-(5,5-dimethyl-1,3-dioxan-2-yl)-phenyl]-17α-ethinyl-9-estrene-5α,17β-diol in 90 ml of 70% aqueous acetic acid is stirred for 30 minutes at 50° C. After cooling, it is poured into ice water, neutralized by the addition of aqueous ammonia solution and extracted with dichloromethane. Crystallization of the crude product from ethyl acetate/diisopropyl ether yields 5.3 g of 17α-ethinyl-11β-(4-formylphenyl)-17β-hydroxy-4,9-estradien-3-one with a melting point of 197°-198° C.

The basic material is produced in the following way:
a) After successive addition of 37.5 g of 2,2-dimethyl-propane-1,3-diol, 18,75 ml of ortho-formic acid trimethylester and 20 mg of p-toluene sulfonic acid, a solution of 25 g of 4-bromobenzaldehyde in 250 ml of dichloromethane is stirred for 24 hours at room temperature. To finish the compound it is poured into saturated, aqueous NaHCO$_3$solution and extracted with diethylether. Crystallization of the crude product from hexane yields 37.1 g of 4-(5,5-dimethyl-1-,3-dioxan-2-yl)-bromobenzene with a melting point of 62°-64° C.

b) First 0.05 ml of iodomethane and then a solution of 54 g of 4-(5,5-dimethyl-1,3-dioxan-2-yl)-bromobenzene in 270 ml of absolute tetrahydrofurane (THF) are added to a suspension of 4.5 g of magnesium chips in 120 ml of absolute THF at 25° C. so that the internal temperature does not exceed 45° C. After complete solution of the magnesium the mixture is cooled to +5° C. and 1.07 g of CuCl are added in portions to the reaction solution. Stirring continues for 15 minutes, then a solution of 25.4 g of 3,3-(2,2-dimethyl-trimethylenedioxy)-5α,10α-epoxy-9(11)-estren-17β-ol in 250 ml of abs. THF are added drop by drop at a temperature of +5° C. After addition stirring continues for another 2 hours at room temperature, then the reaction solution is poured into a mixture of ice water/aqueous ammonia solution and extracted with ethyl acetate. The oily crude product thus obtained is chromatographed with hexane/ethyl acetate on aluminum oxide (Merck, stage III, neutral). Crystallization of the main fraction from ethyl acetate/diisopropyl ether yields 33.8 g of 3,3-(2,2-dimethyl-trimethylenedioxy)-11β-[4-(5,5-dimethyl-1,3-dioxan-2-yl)-phenyl]-9-estrene-5α,17β-diol with a melting point of 218°-220° C.

$[\alpha]_D^{25} + 36.0°$ (CH$_2$Cl$_2$, c=0.505).

c) A suspension of 12.7 g of the producted obtained in b), 74 ml of cyclohexanone, 7.1 g of aluminum isopropylate and 494 ml of toluene are heated for 4 hours with reflux, and approximately one-third of the solvent is distilled off. After cooling the mixture is poured into ice water, the resulting emulsion filtered through Celite, the filter residue thoroughly washed with ethyl acetate, the organic phase of the filtrate separated, the same dried over Na$_2$SO$_4$ and concentrated. Chromatography over Al$_2$O$_3$, neutral, stage III, with hexane/ethyl acetate and crystallization of the main fraction from hexane/ethanol yields 9.6 g of 3,3-(2,2-dimethyl-trimethylenedioxy)-11β-[4-(5,5-dimethyl-1,3-dioxan-2-yl)-phenyl]-5α-hydroxy-9-estren-17-one with a melting point of 209°-211° C.

$[\alpha]_D^{25} + 62.3°$ (CH$_2$C$_2$, c=0.510).

d) Abs. THF (495 ml) is saturated with acetylene for 30 minutes at 0° C. 100 ml of a 15% solution of n-butyllithium in hexane are dripped in and then a solution containing 8.75 g of the ketone obtained in c) in 135 ml of THF. The mixture is stirred for 3.5 hours at room temperature, then poured into approximately 2 l of ice water and extracted with ethyl acetate. The oily crude product thus obtained (9.0 g) is put into the final stage without further purification.

EXAMPLE 2

11β-(4-formylphenyl)-17β-hydroxy-17α-(1-propinyl)-4-9-estradien-3-one 20.1 g of 3,3-(2,2-dimethyl-trimethylenedioxy)-11β-[4-(5,5-dimethyl-1,3-dioxan-2-yl)-phenyl]-17α-(1-propinyl)-b 9-estrene-5α,17β-diol are stirred in 83 ml of 70% aqueous acetic acid for 30 minutes at 60° C. and finished in the conditions mentioned in Example 1. Crystallization of the crude product from methylene chloride/diisopropyl ether yields 10.6 g of the title compound with a melting point of 207°-208° C.

The basic material is produced in the following way:
Abs. THF (1040 ml) is saturated by passing methylacetylene into it for 30 minutes at 0° C. 84.4 ml of a 15% solution of n-butyllithium is then added drop by drop at 0° to +5° C., the mixture stirred for 15 minutes and a solution of 19.4 g of 3,3-(2,2-dimethyl-trimethylenedioxy)-11β-[4-(5,5-dimethyl-1,3-dioxan-2-yl)-phenyl]-5α-hydroxy-9-estren-17-one (cf. example 1 c) is then added drop by drop. The mixture is stirred for another 60 minutes at room temperature, poured into ice water and extracted with ethyl acetate. The crude product (20.1 g) is put into the final stage without further purification.

EXAMPLE 3

11β-(4-formylphenyl)-17α-hydroxy-13α-methyl-17β-(1-propinyl)-4-9-gonadien-3-one 1.1 g of 3,3-(2,2-dimethyl-trimethylenedioxy)-11β-[4-(5,5-dimethyl-1,3-dioxan-2-yl)-phenyl]-13α-methyl-17β-(1-propinyl)-9-gonene-5α,17α-diol are made to react with 15 ml of 70% acetic acid at 60° C. in the conditions of Example 1. Chromatography of the crude product on silica gel with hexane/ethyl acetate yields 530 mg of the title compound in an amorphous state.
$[\alpha]_D^{25} + 437.8°$ (CHCl$_3$, c=0.5).

The basic material is produced in the following way:

a) 4.0 g of the ketone obtained in 1 c) and dissolved in 600 ml of dioxane is irradiated in a quartz-glass immersion apparatus for 35 minutes at 25° C. with a high-pressure Hg lamp (Philips HPK 125). The solvent is then removed in a water-jet vacuum and the oily residue is chromatographed on Al$_2$O$_3$ (Merck, neutral, stage III) with hexane/ethyl acetate. Crystallization of the main fraction from diisopropylether yields 2.05 g of 3,3-(2,2-dimethyl-trimethylenedioxy)-11β-[4-(5,5-dimethyl-1,3-dioxan-2-yl)-phenyl]-5α-hydroxy-13α-methyl-9-gonen-17-one with a melting point of 185°-187° C.
$[\alpha]_D^{25} + 27.3°$ (CH$_2$Cl$_2$, c=0.53).

b) 1.9 g of the ketone obtained in a) are made to react with methylacetylene in the conditions of Example 2 a). Chromatography of the crude product on Al$_2$O$_3$ with hexane/ethyl acetate and crystallization of the main fraction from CH$_2$Cl$_2$/ethyl acetate yield 1.22 g of 3,3-(2,2-dimethyl-trimethylenedioxy)-11β-[4-(5,5-dimethyl-1,3-dioxan-2-yl)-phenyl]-13α-methyl-17β-(1-propinyl)-9-gonene-5α,17α-diol with a melting point of 240°-243° C.
$[\alpha]_D^{25} + 35.2°$ (CH$_2$Cl$_2$, c=0.5).

EXAMPLE 4

11β-(3-formylphenyl)-17β-hydroxy-17α-(1-propinyl)-4-9-estradien-3-one 2.7 g of 3,3-(2,2-dimethyl-trimethylenedioxy)-11β-[3-(5,5-dimethyl-1,3-dioxan-2-yl)-phenyl]-17α-(1-propinyl)-9-estrene-5α,17β-diol are separated in the conditions of Example 1 with 30 ml of 70% acetic acid. Crystallization of the crude product thus obtained from dichloromethane/acetone yields 1.15 g of the title compound with a melting point of 260°-262° C.
$[\alpha]_D^{25} - 60.2°$ (pyridine, c=0.35).

The basic material is produced in the following way:

a) After crystallization from hexane 31.7 ml of 3-bromobenzaldehyde, 75 g of 2,2-dimethyl-propane-1,3-diol, 37.6 ml of orthoformic acid trimethylester and 50 mg of p-toluene sulfonic acid in 500 ml of dichloromethane yield in the conditions of Example 1 a) 78.0 g of 3-(5,5-dimethyl-1,3-dioxan-2-yl)-methylbromobenzene with a melting point of 42°-43° C.

b) After chromatography over Al$_2$O$_3$ with hexane/ethyl acetate 15.0 g of 3,3-(2,2-dimethyl-trimethylenedioxy)-5α,10α-epoxy-9(11)-estren-17β-ol, 62.2 g of the ketal obtained in a), 4.82 of magnesium, 0.08 ml of iodomethane and 1.02 g of CuCl in 420 ml of THF yield in the conditions of Example 1 b) 19.6 g of 3,3-(2,2-dimethyl-trimethylenedioxy)-11β-[3-(5,5-dimethyl-1,3-dioxan-2-yl)-phenyl]-9-estrene-5α,17β-diol in the form of a colorless oil.

c) Oppenauer oxidation of the product obtained in b) (18.0 g), 10.3 g of aluminum isopropylate, 112 ml of cyclohexanone, 560 ml of toluene in the conditions of Example 1 c) and after crystallization of the crude product from diisopropyl ether yields 13.8 g of the 17-ketone with a melting point of 195°-197° C.
$[\alpha]_D^{25} + 51.2°$ (CH$_2$Cl$_2$, c=0.5).

d) 2.5 g of the ketone obtained in c) are made to react with the lithium derivative of methylacetylene in the conditions of Example 2 a). The crude product (2.7 g) is put into the final stage without further purification.

EXAMPLE 5

11β-(3-formylphenyl)-17α-hydroxy-13α-methyl-17β-(1-propinyl)-4-9-gonadien-3-one

After chromatography on silica gel with hexane/acetone, acid hydrolysis of 1.0 g of 3,3-(2,2-dimethyl-trimethylenedioxy)-11β-[3-(5,5-dimethyl-1,3-dioxan-2-yl)-phenyl]-13α-methyl-17β-(1-propinyl)-9-gonene-5α,17α-diol yields, analogous to Example 1, 560 mg of the title compound in an amorphous state.
$[\alpha]_D^{25} + 326.0°$ (CHCl$_3$, c=0.525).

The basic material is produced in the following way:

a) 3.5 g of the ketone obtained in Example 4 c) dissolved in 525 ml of dioxane is irradiated in the conditions described in Example 3 a). Chromatography of the crude product on Al$_2$O$_3$ with hexane/ethyl acetate and crystallization of the main fraction from diisopropyl ether yield 1.97 g of 3,3-(2,2-dimethyl-trimethylenedioxy)-11β-[3-(5,5-dimethyl-1,3-dioxan-2-yl)-phenyl]-5α-hydroxy-13α-methyl-9-gonen-17-one with a melting point of 209°-211° C.
$[\alpha]_D^{25} + 27°$ (CH$_2$Cl$_2$, c=0.525).

b) After chromatography and crystallization from ethyl acetate/diisopropyl ether reaction of the product obtained in a) (1.8 g) with methylacetylene in the conditions of Example 2 a) yields 1.12 g of 3,3-(2,2-dimethyl-trimethylenedioxy)-11β-[3-(5,5-dimethyl-1,3-dioxan-2-yl)-phenyl]-13α-methyl-16β-(1-propinyl)-9-gonene-5α,17α-diol with a melting point of 167°-170° C.
$[\alpha]_D^{25} + 35.2°$ (CH$_2$Cl$_2$, c=0.525).

EXAMPLE 6

11β-(4-acetylphenyl)-17β-hydroxy-17α-(1-propinyl)-4,9-estradien-3-one

Reaction of 2.36 g of 3,3-(2,2-dimethyl-trimethylenedioxy-11β-[4-{1,1-(2,2-dimethyltrimethylenedioxy)-ethyl}-phenyl]-5α-hydroxy-9-estren-17-one with methylacetylene in the conditions of Example 2 a) and subsequent acetic acid hydrolysis of the crude product in the conditions of Example 1 yield 1.14 g of the title compound with a melting point of 151°-154° C. (from hexane/acetone).
$[\alpha]_D^{25} + 117.1°$ (ChCl$_3$, c=0.525).

The basic material is produced in the following way:

a) After chromatography of the crude product on Al$_2$O$_3$ with hexane/ethyl acetate 50.0 g of 4-bromoacetophenone, 75 g of 2,2-dimethylpropane-1,3-diol, 37.6 ml of orthoformic acid trimethylester and 30 mg of p-toluene sulfonic acid in 500 ml of dichloromethane yield in the conditions of Example 1 a) and 4 a) 73 g of the ketal in the form of a colorless oil.

b) After chromatography 14.1 g of 3,3-(2,2-dimethyl-trimethylenedioxy)-5α,10α-epoxy-9(11)-estren-17β-ol, 4.12 g of magnesium, 55.92 g of the bromoketal obtained in a), 0.05 ml of iodomethane and 874 mg of CuCl in a total of 390 ml of THF yield in the conditions of Example 1 b) 14.6 g of adduct in the form of a colorless oil.

c) With Oppenauer oxidation analogue to Example 1 c) and after crystallization of the crude product from ethyl acetate/diisopropyl ether, 12.8 g of the Grignard product obtained in b) yield 11.5 g of the 17-ketone with a melting point of 211°–215° C.

EXAMPLE 7

11$\beta$-(4-acetylphenyl)-17$\alpha$-hydroxy-13$\alpha$-methyl-17$\beta$-(1-propinyl)-4,9-gonadien-3-one Irradiation of 4.0 g of the ketone obtained in Example 6 c) in the conditions of Example 3 a), reaction of the product thus obtained with methylacetylene in the conditions of Example 2 a) and subsequent acetic acid separation analogue to 1 yield 1.09 g of amorphous 11$\beta$-(4-acetylphenyl)-17$\alpha$-hydroxy-13$\alpha$-methyl-17$\beta$-(1-propinyl)-4,9-gonadien-3-one.
$[\alpha]_D^{25} +420.1°$ (CHCl$_3$, c=0.525).

EXAMPLE 8

17$\beta$-hydroxy-11$\beta$-[4-(3-oxo-1(E)-propenyl)-phenyl]-17$\alpha$-(1-propinyl)-4,9-estradien-3-one A solution of 750 mg of 17$\beta$-hydroxy-11$\beta$-[4-(3-hydroxy-1-(E)-propenyl)-phenyl]-17$\alpha$-(1-propinyl)-4,9-estradien-3-one in 20 ml of dichloromethane is stirred after the addition of 4.0 g of manganese dioxide at room temperature for 15 minutes. The mixture is then filtered with Celite and the filtrate concentrated. This yields 620 mg of amorphous 17$\beta$-hydroxy-11$\beta$-[4-(3-oxo-1(E)-propenyl)-phenyl]-17$\alpha$-(1-propinyl)-4,9-estradien-3-one.
$[\alpha]_D^{25} +218.6°$ (CHCl$_3$, c=0.5).

The basic material is produced in the following way:

a) 81 ml of a 1.6 molar solution of vinylmagnesium bromide in THF are dripped at $-10°$ C. into a solution of 20.0 g of 4 bromobenzaldehyde in 300 ml of absolute THF. After addition the mixture is stirred for 60 minutes at 0° C., poured into ice water and extracted with ethyl acetate. After chromatography on Al$_2$O$_3$ with hexane/ethyl acetate 18.6 g of 4-(1-hydroxy-2-propenyl)-bromobenzene are obtained in the form of colorless oil.

b) The product obtained in a) (18.6 g) is dissolved in 100 ml of THF and stirred for 3 hours at room temperature after the addition of 25 ml of dihydropyrane and 0.02 ml of POCl$_3$. The mixture is then poured into saturated NaHCO$_3$ and extraction done with diethyl ether. Chromatography of the crude product on Al$_2$O$_3$ with hexane/ethyl acetate yields 19.2 g of 4-[3-(tetrahydropyran-2-yloxy)-1(E)-propenyl]-bromobenzene in the form of colorless oil.

c) A Grignard reagent is made from 920 mg of magnesium in 15 ml of abs. THF, 0.05 ml of iodomethane and 13.0 g of the bromide obtained in b) in 50 ml of THF and, after the addition of 195 mg CuCl, made to react in the conditions of Example 1 b) with 5.0 g of 3,3-(2,2-dimethyl-trimethylenedioxy)-5$\alpha$,10$\alpha$-epoxy-9(11)estren-17$\beta$-ol in 50 ml of THF. The reaction time amounts to 24 hours in this case. Chromatographic purification of the crude product yields 4.5 g of the adduct in the form of a yellowish oil.

d) With Oppenauer oxidation of the adduct obtained in c) analogue to Example 1 c) and after chromatography on Al$_2$O$_3$ with hexane/ethyl acetate 3.3 g of educt yield 2.94 g of the 17-ketone in the form of oil.

e) Reaction of the ketone obtained in d) (2.9 g) with methylacetylene in the conditions of Example 2 a) and, in the conditions of Example 1, acid separation of the crude product thus obtained yield 960 mg of 17$\beta$-hydroxy-11$\beta$-[4-(3-hydroxy-1(E)-propenyl)-phenyl]-17$\alpha$-(1-propinyl)-4,9-estradien-3-one in the form of compact foam.
$[\alpha]_D^{25} +142.4°$ (CHCl$_3$, c=0.5).

EXAMPLE 9

3.65 g of hydroxylamine hydrochloride are added ice-cooled in portions to a solution of 4.07 g of 11$\beta$-(4-formylphenyl)-17$\beta$-hydroxy-17$\alpha$-(1-propinyl)-4,9-estradien-3-one (cf. Example 2) in 60 ml of pyridine. After addition the mixture is stirred for 30 minutes at $+5°$ C., poured into a mixture of ice water and 0.5N hydrochloric acid and extracted with dichloromethane. Fractionated crystallization of the crude product (4.53 g) from ethyl acetate yields the following:

a) 2.17 g of 11$\beta$-[4-(anti-hydroxyiminomethyl)-phenyl]-17$\beta$-hydroxy-17$\alpha$-(1-propinyl)-4,9-estradien-3-one-anti-oxime with a melting point of 242°–244° C.

b) 880 mg of 11$\beta$-[4-(anti-hydroxyiminomethyl)-phenyl]-17$\beta$-hydroxy-17$\alpha$-(1-propinyl)-4,9-estradien-3-one-syn-oxime with a melting point of 248°–251° C.

EXAMPLE 10

11$\beta$-(4-formylphenyl)-17$\beta$-hydroxy-17$\alpha$-(3-hydroxy-1(Z)-propenyl)-4,9-estradien-3-one After chromatographic purification the reaction of 5.71 g of 3,3-(2,2-dimethyl-trimethylenedioxy)-11$\beta$-[4-(5,5-dimethyl-1,3-dioxan-2-yl)-phenyl]-17$\alpha$-[3-(tetrahydropyran-2-yloxy)-1(Z)-propenyl]-9-estrene-5$\alpha$,17$\beta$-diol with 70 ml of 70% acetic acid in the conditions of Example 1 yields 2.3 g of 11$\beta$-(4-formylphenyl)-17$\beta$-hydroxy-17$\alpha$-(3-hydroxy-1(Z)-propenyl)-4,9-estradien-3-one in the form of a compact foam.
$[\alpha]_D^{25} +221.1°$ (CHCl$_3$, c=0.520).

The basic material is produced in the following way:

a) 6.35 g of 3-(tetrahydropyran-2-yloxy)-1-propine in 115 ml of abs. THF and 31.6 ml of a 15% solution of n-butyllithium in hexane are used to produce the lithium-organic compound at 0° C., a solution of 5.1 g of the ketone obtained in example 1 c) in 70 ml of abs. THF being dripped into the mixture at 0° to $+5°$ C. The mixture is then stirred at room temperature for 3 hours, poured into ice water and extracted with ethyl acetate. The crude product is chromatographed on neutral aluminum oxide with hexane/ethyl acetate. 7.2 g of 3,3-(2,2-dimethyl-trimethylenedioxy)-11$\beta$-[4-(5,5-dimethyl-1,3-dioxan-2-yl)-phenyl]-17$\alpha$-[3-(tetrahydropyran-2-yloxy)-1-propinyl]-9-estrene-5$\alpha$,17$\beta$-diol are obtained in the form of an oily main fraction.

b) A solution of 5.75 g of the product obtained in a) in 75 ml of THF is hydrated at room temperature and normal pressure after addition of 5 ml of pyridine and 560 mg of palladium/barium sulfate (10% Pd). When the absorption of water comes to a stop, the mixture is filtered from the catalyst, and the filtrate is concentrated. 5.71 g of 3,3-(2,2-dimethyl-trimethylenedioxy)-11$\beta$-[4-(5,5-dimethyl-1,3-dioxan-2-yl)-phenyl]-17$\alpha$-[3-(tetrahydropyran-2-yloxy)-1(Z)-propenyl]-9-estrene-5$\alpha$,17$\beta$-diol are obtained in the form of oil.

EXAMPLE 11

11β-(4-formylphenyl)-17β-hydroxy-13α-methyl-17α-(1-propinyl)-4,9-gonadien-3-one 420 mg of 3,3-(2,2-dimethyl-trimethylenedioxy)-11β-[4-(5,5-dimethyl-1,3-dioxan-2-yl)-phenyl]-13α-methyl-17α-(1-propinyl)-9-gonene-5α,17β-diol is made to react with 6.5 ml of 70% acetic acid at 60° C. under the conditions of example 1. Chromatography of the crude product on silica gel with hexane/ethyl acetate yields 180 mg of the title compound in the form of yellowish foam. $[\alpha]_D^{25}$ +162 5° (CHCl$_3$, c=0.5).

The basic material is produced in the following way:

After chromatography the addition reaction with methylacetylene described in 3 b) yields 480 mg of 3,3-(2,2-dimethyltrimethylenedioxy)-11β-[4-(5,5-dimethyl-1,3-dioxan-2-yl)phenyl]-13α-methyl-17α-(1-propinyl)-9-gonene-5α,17β-diol as a non-polar by-product in the form of a yellowish oil.

EXAMPLE 12

11β-(4-acetylphenyl)-17β-hydroxy-9α,10α-methylene-17α-(1-propinyl)-4-estren-3-one.

Reaction of 6.2 g of 3,3-(2,2-dimethyl-trimethylenedioxy)-11β-[4-{(1,1-(2,2-dimethyl-trimethylenedioxy)-ethyl}-phenyl]-9α,10α-methylene-17α-(1-propinyl)-estrane-5α,17β-diol with 60 ml of 70% aqueous acetic acid in the conditions of Example 1) yields, after crystallization of the crude product from ethyl acetate/diisopropylether, 3.14 g of the title compound with a melting point of 233°-235° C.
$[\alpha]_D^{25}$ = +36.4° (CHCl$_3$, c=0.505).

The basic material is produced in the following way:

a) 9.6 ml of glacial acetic acid are slowly dripped into a suspension of 96 g of zinc dust in 360 ml of abs. THF and 1.73 g of cupric acetate at room temperature. The mixture is subsequently stirred for 15 minutes at 25° C., and then 3.36 ml of triethylamine are dripped into the suspension. Afterward a solution of 21.0 g of 3,3-(2,2-dimethyl-trimethylenedioxy)-11β-[4-{(1,1-(2,2-dimethyltrimethylenedioxy)-ethyl}-phenyl]-9-estrene-5α,17β-diol in 190 ml of abs. THF is dripped in within 15 minutes. Following thereon 67.2 ml of dibromomethane are added drop by drop so that the reaction solution heats up until it is slightly boiling. After addition (approx. 45 minutes) the mixture is heated for another 2 hours with slight reflux and then stirred for another 12 hours at room temperature.

To finish the product approx. 300 ml of saturated NH$_4$Cl solution is dripped iced-cooled into the reaction suspension, the mixture then being diluted with methylene chloride, filtered with Celite, and the filtrate washed several times with aqueous ammonia. The crude product is chromatographed on Al$_2$O$_3$ (Merck, neutral, stage III) with hexane/ethyl acetate. Crystallization of the main fraction from ethyl acetate yields 13.4 g of 3,3-(2,2-dimethyl-trimethylenedioxy)-11β-[4-{(1,1-(2,2-dimethyltrimethylenedioxy)-ethyl}-phenyl]-9α,10α-methylene-estrane-5α,17β-diol with a melting point of 170°-174° C.
$[\alpha]_D^{25}$ = +55.2° (CH$_2$Cl$_2$, c=0.510).

b) After chromatography on Al$_2$O$_3$ with hexane/ethyl acetate and crystallization from hexane/diisopropyl ether, Oppenauer oxidation of 5.9 mg of the product obtained in a) yields in the conditions of Example 1 c) 5.2 g of the 17-ketone with a melting point of 206°-208° C.
$[\alpha]_D^{25}$ = +55.2° (CH$_2$Cl$_2$, c=0.515).

c) After crystallization of the crude product from ethyl acetate/diisopropyl ether, reaction of 5.3 g of the ketone obtained in b) with methylacetylene in the conditions of Example 2 a) yields 4.85 g of the basic product required for the final stage and having a melting point of 146°-149° C.
$[\alpha]_D^{25}$ = −8.8° (CH$_2$Cl$_2$, c=0.510).

EXAMPLE 13

11β-(4-acetylphenyl)-17β-hydroxy-17α-(3-hydroxy-1(Z)-propenyl)-9α,10α-methylene-4-estren-3-one.

Reaction of 5.9 g of 3,3-(2,2-dimethyl-trimethylenedioxy)-11β-[4-{1,1-(2,2-dimethyl-trimethylenedioxy)-ethyl}-phenyl]-9α,10α-methylene-17α-[3-(tetrahydropyran-2-yloxy)-1(Z)-propenyl]-estrane-5α,17β-diol with 58 ml of 70% aqueous acetic acid analogue to Example 1 yields, after crystallization of the crude product from acetone, 2.16 g of the title compound with a melting point of 145°-149° C.
$[\alpha]_D^{25}$ = +95.8° (CHCl$_3$, c=0.505).

The basic material is produced in the following way:

The ketone (7.5 g) obtained in Example 12 b) is made to react with propargylalcohol-tetrahydropyranyl ether in the conditions of Example 10 a), and the adduct thus obtained is hydrated without further purification in the conditions of Example 10 b). The starting material mentioned above is obtained in the form of colorless oil (5.9 g).

EXAMPLE 14

17β-hydroxy-17α-(1-propinyl)-11β-(4-propionylphenyl)-4,9-estradien-3-one

After crystallization of the crude product from hexane/acetone, treatment of 11.0 g of 3,3-(2,2-dimethyl-trimethylenedioxy)-11β-[4{-1,1-(2,2-dimethyl-trimethylenedioxy)-propyl}-phenyl]-17α-(1-propinyl)-9-estrene-5α,17β-diol with 49 ml of 70% aqueous acetic acid in the conditions of Example 1) yield 6.2 g of the title compound with a melting point of 133°-136° C.
$[\alpha]_D^{25}$ = +123.3° (CHCl$_3$, c=0.565).

The basic material is produced in the following way:

a) After chromatography of the raw product on Al$_2$O$_3$, 66.7 g of 4-bromopropiophenone yield, by ketalization with 100 g of 2,2-dimethyl-propane-1,3-diol, 79.7 g of the ketal in the form of a colorless oil.

b) After chromatography 5.39 g of magnesium, 79.7 g of the ketal obtained in a), 20.4 g of 3,3-(2,2-dimethyl-trimethylenedioxy)-5α,10α-epoxy-9(11)-estren-17β-ol and 1.24 g CuCl in a total of 540 ml of abs. THF yield, in the conditions of Example 1 b), 28.7 g of the adduct in the form of yellowish oil.

c) After chromatography of the raw product, Oppenauer oxidation of the product obtained in b) (28.7 g) yields, analogous to Example 1 c) 27.5 g of the 17-ketone in the form of compact foam.

d) Reaction of the ketone obtained in c) (10.9 g) with methylacetylene in the conditions of Example 2) yields 11.0 g of the basic material required for the final stage in the form of a colorless oil.

EXAMPLE 15

17α-ethinyl-17β-hydroxy-11β-(4-propionylphenyl)-4,9-estradien-3-one

After crystallization of the crude product from ethyl acetate/diisopropyl ether, reaction of 5.9 g of 17α-ethinyl-3,3-(2,2-dimethyl-trimethylenedioxy)-11β-[4-{1,1-(2,2-dimethyl-trimethylenedioxy)propyl}-phenyl]-9-estrene-5α,17β-diol with 25 ml of 70% acetic acid yields, in the conditions of Example 1, 1.99 g of the title compound with a melting point of 114°–117° C.
$[α]_D^{25} = +122.3°$ (CHCl$_3$, c=0.520).

The basic material is produced in the following way:
The ketone obtained in Example 14 c) (5.8 g) is made to react in the conditions of Example 2, acetylene being used instead of propine, however. This yields 5.9 g of the ethinylation product in the form of colorless oil that is used, without further purification, for the separation of acetic acid described above.

EXAMPLE 16

17α-bromoethinyl-17β-hydroxy-11β-(4-propionylphenyl)-4-9-estradien-3-one

A suspension of 1.0 g of 17α-ethinyl-17β-hydroxy-11β-(4-propionylphenyl)-4,9-estradien-3-one, 60 mg of silver nitrate and 700 mg of N-bromosuccinimide in 40 ml of acetone and 6 ml of water is stirred for 40 minutes at 25° C. The mixture is then poured into an NH$_3$ solution and extracted with ethyl acetate. Crystallization of the crude product from ethyl acetate yields 720 mg of the title compound with a decomposition point of 132° C.
$[α]_D^{25} = +57.2°$ (CHCl$_3$, c=0.510).

EXAMPLE 17

11β-(4-acetylphenyl)-17β-hydroxy-17α-(3-hydroxy-1(Z)-propenyl)-4,9-estradien-3-one.

a) After chromatography of the raw product on Al$_2$O$_3$ with hexane/ethyl acetate 9.74 g of propargylalcohol-tetrahydropyranyl ether, 56.4 ml of a 15% solution of n-butyllithium in hexane and 10.01 g of 3,3-(2,2-dimethyl-trimethylenedioxy)-11β-[4-{1,1-(2,2-dimethyl-trimethylenedioxy)-ethyl}-phenyl]-5α-hydroxy-9-estren-17-one (cf. Example 6 c for its manufacture) yield, by the method of Example 10 a), 11.66 g of the adduct as an oily mixture of diastereomer THP ether.

b) Partial hydration of 8.66 g of the product obtained in a) by the method of Example 10 b) and subsequent acetic acid separation of the crude product analogous to Example 1) yield, after chromatographic purification and crystallization from ethanol, 2.55 g of 11β-(4-acetylphenyl)-17β-hydroxy-17α-3-hydroxy-1(Z)-propenyl-4,9-estradien-3-one with a melting point of 116°–118 ° C.
$[α]_D^{25} = +193.2°$ (CH$_2$Cl$_2$, c=0.520).

EXAMPLE 18

11β-(4-acetylphenyl)-17β-hydroxy-17α-(3-hydroxypropyl)-4,9-estradien-3-one

After addition of 320 mg of palladium coal (10%) a solution of 3.6 g of the product obtained in 17 a) in 30 ml of ethanol is hydrated at room temperature and normal pressure until a standstill is reached. After filtering off the catalyst the mixture is concentrated, the oily crude product (3.6 g) placed in 20 ml of 70% acetic acid and stirred for 45 minutes at 60° C. Finishing analogous to Example 1 and chromatography on silica gel with hexane/ethyl acetate yield 1.6 g of 11β-(4-acetylphenyl)-17β-hydroxy-17α-(3-hydroxy-propyl)-4,9-estradien-3-one in the form of a compact foam.
$[α]_D^{25} = +177.0°$ (CH$_2$Cl$_2$, c=0.510).

EXAMPLE 19

3-[11β-(4-acetylphenyl)-17β-hydroxy-3-oxo-4,9-estradien-17α-yl]-propionic acid actone A solution of 1.51 g of the product obtained in Example 18 in 63 ml of acetone is mixed, ice-cooled, with 2.1 ml of Jones' reagent drop by drop. The mixture is then stirred for 15 minute at room temperature, the reaction solution poured into water, neutralized by the addition of aqueous ammonia solution and extracted with dichloromethane. Crystallization of the crude product from hexane/ethyl acetate yields 1.06 g of 3-[11β-(4-acetylphenyl)-17β-hydroxy-3-oxo-4,9-estradien-17α-yl]-propionic acid acetone with a melting point of 243°–245° C.
$[α]_D^{25} = +149.2°$ (CH$_2$Cl$_2$, c=0.50).

EXAMPLE 20

11β-(4-acetylphenyl)-15β,17β-dihydroxy-17α-(1-propinyl)-4,9-estradien-3-one 500 ml of a sterile nutrient solution containing 1% glucose, 0.1% yeast extract, 0.1% beef extract, 0.2% tryptose, 1.5% agar with a pH value of 7.2 are inoculated with a 10 day-old inclined agar culture of Streptomyces platensis (NRRL 2364) and agitated for 60 hours at 30° C. 300 ml of this preliminary culture are placed in a 10 l fermenter containing 5 l of sterile medium of the composition indicated above. The culture is developed at 29° C. at a speed of 220 rpm with 5 l of air/min. After 12 hours 1.0 g of 11β-(4-acetylphenyl)-17β-hydroxy-17α-(1-propinyl)-4,9-estradien-3-one in 60 ml of dimethylformamide is added after prior sterile filtration. The substrate concentration amounts to 200 mg/l . The reaction is checked by thin-layer chromatography. The fermentation is stopped after 36 hours of contact time. The culture broth is extracted with methyl isobutyl ketone and the extract concentrated in a vacuum at 30°–40° C. The residue thus obtained is washed with hexane to remove the antifoam agent (silicone SH). The substance is then chromatographed on silica gel with hexane/ethyl acetate. Crystallization of the main fraction from ethyl acetate/diisopropyl ether yields 400 mg (38.4% of the theoretical amount) of the title compound with a melting point of 152°–154° C.

EXAMPLE 21

11β-(4-acetylphenyl)-16α,17β-dihydroxy-17α-(1-propinyl)-4,9-estradien-3-one

11β-(4-acetylphenyl)-17β-hydroxy-17α-(1-propinyl)-4,9-estradien-3-one (1.0 g) are used for fermentation with Streptomyces toyocaensis (DSM 40030) in the conditions of Example 20. The fermentation time amounts to 95 hours and the contact time 81 hours. Purification with column chromatography and crystallization from ethyl acetate/hexane yield 370 mg of the title compound with a melting point of 225°–229° C.

EXAMPLE 22

11β-(4-acetylphenyl)-6α,17β-dihydroxy-17α-(1-propinyl)-4,9-estradien-3-one

11β-(4-acetylphenyl)-17β-hydroxy-17α-(1-propinyl)-4,9-estradien-3-one (1.0 g) is used for fermentation with Nigrospora sphaerica (CBS 98469) in the conditions of Example 20. A medium with the following compositions is used in this connection: 3% glucose, 1% cornsteep, 0.2% NaNO$_3$, 0.1% KH$_2$PO$_4$, 0.2% K$_2$HPO$_4$, 0.05% MgSO$_4$, 0.002% FeSO$_4$, 0.05% KCl with a pH value of 6.0. The fermentation time amounts to 112 hours, the contact time 100 hours. Chromatographic purification yields 235 mg of the title compound with a melting point of 148°–152° C. (from ethyl acetate).

EXAMPLE 23

11β-(4-acetylphenyl)-7α,17β-dihydroxy-17α-(1-propinyl)-4,9-estradien-3-one

After chromatographic purification fermentation of 1.0 g of 11β-(4-acetylphenyl)-17β-hydroxy-17α-(1-propinyl)-4,9-estradien-3-one in the conditions of Example 20 and with the use of the medium in Example 22 with Neurospora crassa (ATCC 9278) yields 196 mg of the title compound with a melting point of 156°–159° C. (from hexane/ethyl acetate). In this case the fermentation time amounts to 123 hours, the contact time 112 hours.

EXAMPLE 24

11β-(4-acetylphenyl)-6β-chloro-17β-hydroxy-17α-(1-propinyl)-4,9-estradien-3-one

A solution consisting of 140 mg of the 11β-(4-acetylphenyl)-6α,17β-hydroxy-17α(1-propinyl)-4,9-estradien-3-one obtained in Example 22 in 3 ml of dichloromethane, 0.02 ml of pyridine and 0.4 ml of carbon tetrachloride is stirred for 2 hours at +5° C. after the addition of 840 mg of triphenylphosphine. Afterwards the mixture is poured into a NH4Cl solution and extracted with dichloromethane. The crude product is chromatographed over silica gel with hexane/ethyl acetate. This yields 116 mg of the title compound in the form of an amorphous powder with a pseudo melting point of 140°–144° C.

EXAMPLE 25

11β-(4-acetylphenyl)-17β-hydroxy-6-β-methyl-17α-(1-propinyl)-4,9-estradien-3-one 570 mg of cuprous iodide are added in portions to 5.2 ml of a 5% solution of methyllithium in diethyl ether at 0° C. After complete solution of the copper salt, 640 mg of 11β-(4-acetylphenyl)-17β-hydroxy-17α-(1-propinyl)-6α-tosyloxy-4,9-estradien-3-one in 5 ml of THF and 5 ml of diethyl ether are added at −20° C. and subsequently stirred for 60 minutes at −20° to −10° C. To finish, the mixture is poured into an aqueous ammonia solution and extracted with ethyl acetate. Chromatography on silica gel and crystallization of the main fraction from diisopropyl ether yields 360 mg of the title compound with a melting point of 129°–131° C.

The basic material is produced in the following way:

A solution consisting of 560 mg of 11β-(4-acetylphenyl)-6α,17β-dihydroxy-17α-(1-propinyl)-4,9-estradien-3-one in 4.5 ml of pyrridine are mixed, ice-cooled, with 960 mg of p-toluene sulfonic acid chloride and stirred for 5 hours at +5° C. The mixture is then poured into 30 ml of 0.5N aqueous hydrochloric acid and extracted a number of times with ethyl acetate. The extracts are washed with water and saturated NaHCO3 solution, dried over Na2SO4 and concentrated. This yields a yellowish oil (640 mg) that can be used in the reaction above without further purification.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 13-alkyl-11β-phenyl-gonane of the formula

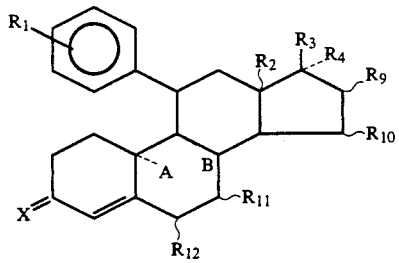

wherein

A and B together represent oxygen, $CH_2$ or a second bond between carbon atoms 9 and 10, X is oxygen or hydroxyimino, N~OH, $R_1$ is alkyl, alkenyl or alkynyl of up to 8 carbon atoms, each of which contains the grouping $$\overset{X}{\underset{}{\overset{\|}{-C-}}},$$

wherein X is as defined above, $R_2$ is methyl or ethyl in the α or β position, in the case of $R_2$ methyl or ethyl in the α-position, $R_3/R_4$ is $-OR_5/-C\equiv C-Y$ $-C\equiv C-Y/-OR_5$ $-OR_5/-\underset{O}{\overset{\|}{C}}-CH_2-R_6$ $-\underset{O}{\overset{\|}{C}}-CH_2R_6/-OR_5$ $-CH_3/-\underset{O}{\overset{\|}{C}}-CH_2-R_6$ $-\underset{O}{\overset{\|}{C}}-CH_2-R_6/-CH_3$ $-H/-\underset{O}{\overset{\|}{C}}-CH_2-R_6$ $-\underset{O}{\overset{\|}{C}}-CH_2-R_6/-H$ $-OR_5/-(CH_2)_m-CH_2-R_7$ $-(CH_2)_m-CH_2-R_7/-OR_5$ $-OR_5/-CH=CH-(CH_2)_k-CH_2-R_7$ $-CH=CH-(CH_2)_k-CH_2-R_7/-OR_5$ $-OR_8/-H$ $-H/-OR_8$ -continued

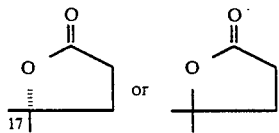

and in the case of $R_2$ methyl or ethyl in the $\beta$ position:
$R_3/R_4$ is

—$OR_5$/—C≡C—Y

—$OR_5$/—C—$CH_2$—$R_6$
         ‖
         O

—C—$CH_2$—$R_6$/—$OR_5$
‖
O

—C—$CH_2$—$R_6$/—$CH_3$
‖
O

—C—$CH_2$—$R_6$/—H
‖
O

—$OR_5$/—$(CH_2)_m$—$CH_2$—$R_7$

—$OR_5$/—CH=CH—$(CH_2)_k$—$CH_2$—$R_7$

—$OR_8$/—H or

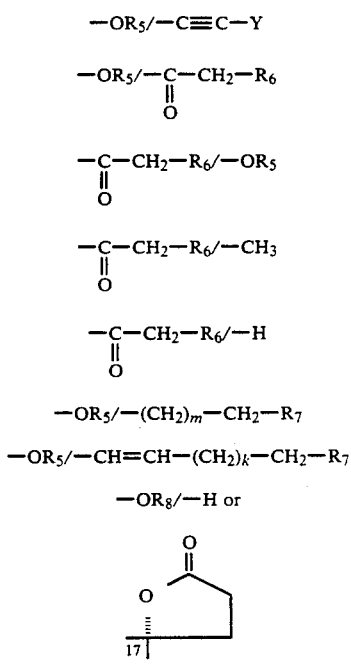

$R_5$ is hydrogen or alkanoyl of 1 to 4 carbon atoms,
Y is hydrogen, chlorine, fluorine, iodine, bromine or alkyl, hydroxyalkyl, alkoxyalkyl or acyloxyalkyl each of 1 to 4 carbon atoms in each alkyl or acyl portion,
$R_6$ is hydrogen, hydroxy or alkyl, O-alkyl or O-acyl each of 1 to 4 carbon atoms,
m is 0, 1, 2 or 3,
$R_7$ is hydroxy, cyano or O-alkyl or O-acyl each of 1 to 4 carbon atoms
k is 0, 1 or 2,
$R_8$ is hydrogen or alkyl or acyl each of 1 to 10 carbon atoms,
each of $R_9$, $R_{10}$, $R_{11}$ and $R_{12}$ independently is hydrogen, halogen, hydroxy or alkyl, alkoxy, acyloxy each of 1 to 4 carbon atoms,
acyl is alkanoyl,
and the substituent on the 11$\beta$-phenyl is in the 3- or 4-position.

2. A compound of claim 1, wherein only one of $R_{9-12}$ is not H.

3. A compound of claim 1, wherein X is O.

4. A compound of claim 1, wherein X is N~OH.

5. A compound of claim 1, wherein $R_2$ is in the $\alpha$-position.

6. A compound of claim 1, wherein $R_2$ is in the $\beta$-position.

7. 17$\alpha$-ethinyl-11$\beta$-(4-formylphenyl)-17$\beta$-hydroxy-4,9-estradien-3-one, a compound of claim 1.

8. 11$\beta$-(4-formylphenyl)-17$\beta$-hydroxy-17$\alpha$-(1-propinyl)-4,9-estradien-3-one, a compound of claim 1.

9. 11$\beta$-(4-formylphenyl)-17$\alpha$-hydroxy-13$\alpha$-methyl-17$\beta$-(1-propinyl)-4,9-gonadien-3-one, a compound of claim 1.

10. 11$\beta$-(3-formylphenyl)-17$\beta$-hydroxy-17$\alpha$-(1-propinyl)-4,9-estradien-3-one, a compound of claim 1.

11. 11$\beta$-(3-formylphenyl)-17$\alpha$-hydroxy-13$\alpha$-methyl-17$\beta$-(1-propinyl)-4,9-gonadien-3-one, a compound of claim 1.

12. 11$\beta$-(4-acetylphenyl)-17$\beta$-hydroxy-17$\alpha$-(1-propinyl)-4,9-estradien-3-one, a compound of claim 1.

13. 11$\beta$-(4-acetylphenyl)-17$\alpha$-hydroxy-13$\alpha$-methyl-17$\beta$-(1-propinyl)-4,9-gonadien-3-one, a compound of claim 1.

14. 11$\beta$-(4-formylphenyl)-17$\beta$-hydroxy-17$\alpha$-(3-hydroxypropyl)-4,9-estradien-3-one, a compound of claim 1.

15. 11$\beta$-(4-formylphenyl)-17$\beta$-hydroxy-17$\alpha$-(3-hydroxy-(Z)-propenyl)-4,9-estradien-3-one, a compound of claim 1.

16. 3-[11$\beta$-(4-formylphenyl)-17$\beta$-hydroxy-3-oxo-4,9-estradien-17$\alpha$-yl]propionic acid lactone, a compound of claim 1.

17. 17$\beta$-hydroxy-11$\beta$-[4-(3-oxo-1(E)-propenyl)-phenyl]-17$\alpha$-(1-propinyl)-4,9-etradien-3-one, a compound of claim 1.

18. 11$\beta$-[4-(anti-hydroxyiminomethyl)-phenyl]-17$\beta$-hydroxy-17$\alpha$-(1-propinyl)-4,9-estradien-3-one-anti-oxime, a compound of claim 1.

19. 11$\beta$-[4-(anti-hydroxyiminomethyl)-phenyl]-17$\beta$-hydroxy-17$\alpha$-(1-propinyl)-4,9-estradien-3-one-syn-oxime, a compound of claim 1.

20. 11$\beta$-(4-acetylphenyl)-17$\beta$-hydroxy-17$\alpha$-(3-hydroxy-1(Z)-propenyl)-4,9-estradien-3-one, a compound of claim 1.

21. 11$\beta$-(4-acetylphenyl)-17$\alpha$-hydroxy-17$\beta$-(3-hydroxy-propyl)-13$\alpha$-methyl-4,9-gonadien-3-one, a compound of claim 1.

22. 11$\beta$-(4-acetylphenyl)-17$\beta$-hydroxy-17$\alpha$-methoxymethyl-4,9-estradien-3-one, a compound of claim 1.

23. 11$\beta$-(4-formylphenyl)-17$\alpha$-hydroxy-13$\beta$-methyl-18,19-dinor-4,9-pregnadiene-3,20-dione, a compound of claim 1.

24. 17$\alpha$-acetoxy-11$\beta$-(4-formylphenyl)-13$\alpha$-methyl-18,19-dinor-4,9-pregnadiene-3,20-dione, a compound of claim 1.

25. 11$\beta$-(4-formylphenyl)-17$\beta$-hydroxy-13$\alpha$-methyl-17$\alpha$-(1-propinyl)-4,9-gonadien-3-one, a compound of claim 1.

26. 11$\beta$-(4-acetylphenyl)-17$\beta$-hydroxy-9$\alpha$,10$\alpha$-methylen-17$\alpha$(1-propinyl)4-estren-3-one, a compound of claim 1.

27. 11$\beta$-(4-acetylphenyl)-17$\beta$-hydroxy-17$\alpha$-(3-hydroxy-1(Z)-propenyl)-9$\alpha$,10$\alpha$methylen-4-estren-3-one, a compound of claim 1.

28. 17$\beta$-hydroxy-17$\alpha$-(1-propinyl)-11$\beta$-(4-propionylphenyl)-4,9-estradien-3-one, a compound of claim 1.

29. 17$\alpha$-ethinyl-17$\beta$-hydroxy-11$\beta$-(4-propionylphenyl)-4,9-estradien-3-one, a compound of claim 1.

30. 17$\alpha$-bromoethinyl-17$\beta$-hydroxy-11$\beta$-(4-propionylphenyl)-4,9-estradien-3-one, a compound of claim 1.

31. 11$\beta$-(4-acetylphenyl)-17$\beta$-hydroxy-17$\alpha$-(3-hydroxypropyl)-4,9-estradien-3-one, a compound of claim 1.

32. 3-[11β-(4-acetylphenyl)-17β-hydroxy-3-oxo-4,9-estradien-17α-yl]4-propionic acid lactone, a compound of claim 1.

33. 11β-(4-acetylphenyl)-15β, 17β-dihydroxy-17α-(1-propinyl)-4,9-estradien-3-one, a compound of claim 1.

34. 11β-(4-acetylphenyl)-16α,17β-dihydroxy-17α-(1-propinyl)-4,9-estradien-3-one, a compound of claim 1.

35. 11β-(4-acetylphenyl)-6α,17β-dihydroxy-17α-(1-propinyl)-4,9-estradien-3-one, a compound of claim 1.

36. 11β-(4-acetylphenyl)-7α,17β-dihydroxy-17α-(1-propinyl)-4,9-estradien-3-one, a compound of claim 1.

37. 11β-(4-acetylphenyl)-6β-chloro-17β-hydroxy-17α-(1-propinyl)-4,9-estradien-3-one, a compound of claim 1.

38. 11β-(4-acetylphenyl)-17β-hydroxy-6β-methyl-17α-(1-propinyl)-4,9-estradien-3-one, a compound of claim 1.

39. 17β-hydroxy-17α-(3-hydroxy-1(Z)-propenyl)-11β-(4-propionyl-phenyl)-4,9-estradien-3-one, a compound of claim 1.

40. 11β-(4-acetylphenyl)-17α-bromoethinyl-17β-hydroxy-4,9-estradien-3-one, a compound of claim 1.

41. A pharmaceutical composition comprising a compound of claim 1 and a carrier.

42. A composition of claim 41, wherein the amount of said compound is 10–100 mg.

43. A method of achieving an antiglucocorticoid effect comprising administering an amount of a compound of claim 1.

44. A method of achieving an antigestagenic effect comprising administering an amount of a compound of claim 1.

45. A method of inducing an abortion comprising administering a compound of claim 1.

* * * * *

UNITED STATES PATENT AND TRADEMARK OFFICE
CERTIFICATE OF CORRECTION

PATENT NO. : 5,089,635

DATED : February 18, 1992

INVENTOR(S) : Gunter Neef, et. al.

It is certified that error appears in the above-identified patent and that said Letters Patent is hereby corrected as shown below:

On the Title page, item [75], Inventors: insert Rudolf Wiechert--.

Signed and Sealed this

Twenty-fifth Day of May, 1993

Attest:

MICHAEL K. KIRK

*Attesting Officer*  *Acting Commissioner of Patents and Trademarks*